United States Patent
Aho et al.

(10) Patent No.: US 7,330,256 B1
(45) Date of Patent: Feb. 12, 2008

(54) SPECTROPHOTOMETRIC SYSTEM WITH REDUCED ANGLE OF INCIDENCE

(75) Inventors: Marc Aho, Mountain View, CA (US); Abdul Rahim Forouhi, Cupertino, CA (US)

(73) Assignee: n&k Technology, Inc., Santa Clara, CA (US)

( * ) Notice: Subject to any disclaimer, the term of this patent is extended or adjusted under 35 U.S.C. 154(b) by 29 days.

(21) Appl. No.: 11/130,638

(22) Filed: May 16, 2005

(51) Int. Cl.
*G01J 3/42* (2006.01)

(52) U.S. Cl. ........................ 356/319; 356/445
(58) Field of Classification Search ........... 356/319, 356/445, 237.5
See application file for complete search history.

(56) References Cited

U.S. PATENT DOCUMENTS

| | | | |
|---|---|---|---|
| 4,784,487 A | 11/1988 | Hopkins, II et al. | 356/326 |
| 4,905,170 A | 2/1990 | Forouhi et al. | 364/556 |
| 5,867,276 A | 2/1999 | McNeil et al. | 356/445 |
| 5,880,831 A * | 3/1999 | Buermann et al. | 356/319 |
| 5,963,329 A | 10/1999 | Conrad et al. | 356/613 |
| 5,991,022 A | 11/1999 | Buermann et al. | 356/319 |
| 6,075,612 A * | 6/2000 | Mandella et al. | 356/445 |
| 6,128,085 A * | 10/2000 | Buermann et al. | 356/369 |
| 6,483,580 B1 | 11/2002 | Xu et al. | 356/300 |
| 6,590,656 B2 | 7/2003 | Xu et al. | 356/369 |
| 2005/0134848 A1* | 6/2005 | Hebert et al. | 356/369 |

* cited by examiner

*Primary Examiner*—Gregory J. Toatley, Jr.
*Assistant Examiner*—Kara E. Geisel
(74) *Attorney, Agent, or Firm*—Lumen Intellectual Property Services, Inc.

(57) ABSTRACT

A system uses reflectance spectrophotometry to characterize a sample having any number of structures. The system uses toroidal mirrors that are shaped in such a way that the angle of reflectance off of the target is small. The small angle of reflectance may allow for simplification of calculations and can result in a faster processing time. In addition, a more accurate measurement can be achieved when the reflected beam is close to normal.

5 Claims, 9 Drawing Sheets side view side view side view front view side view front view front view

US 7,330,256 B1

SPECTROPHOTOMETRIC SYSTEM WITH REDUCED ANGLE OF INCIDENCE

FIELD

The invention relates to optical measurement systems, and, more particularly, to reflectance spectrophotometry.

BACKGROUND

In many industries such as semiconductor manufacturing the characterization of surface structures comprise an important step in verifying the integrity of the manufacturing process. These structures include critical dimensions (CD's), depth, profile, etc. One method of characterizing structures is to use reflectance spectrophotometry.

Reflectance spectrophotometry is a technique where a beam of light is directed toward a target. The light reflects off of the target and is collected in a spectrophotometer. When structures are arranged in a repeating pattern, even if the structures are non-symmetrical, evidence of the structure pattern shows up in the reflected light. By analyzing the properties of the collected light and comparing them to the properties of the original light source, properties of the structures, such as those used in diffraction gratings for example, can be determined.

FIG. 1 shows an example of the disclosure of U.S. Pat. No. 5,991,022 by Buermann, Forouhi, and Mandella, which describes a spectrophotometric apparatus with toroidal mirrors with the desired characteristics stated above. A light source 102 produces a beam of light 104. The beam 104 strikes mirrors 106 A, B in route to illuminating the substrate 108. Light reflected off of the substrate 108 is directed by mirrors 106 C, D into the photodetector 110, which is a spectrophotometer. Data from the photodetector 110 is sent to a computer 112 for processing. The angle of incidence and angle of reflection are shown with $\theta_i$ and $\theta_r$ respectively.

FIG. 2 shows the path of travel for light beam for the system shown in FIG. 1. This is a side view. The light beam 104 comes in from the left side of the page. The light beam 104 strikes the mirror 106B, and is reflected toward the substrate 108. For illustrative purposes only, the substrate 108 and the cross-sectional areas 202, 204 of the light beam 104 are shown in a slight isometric configuration. The cross-sectional area 202 of the beam 104 is not reduced as the beam 104 reflects off of the mirror 106B. Likewise, the cross-sectional area 204 of the beam 104 as the beam 104 strikes the substrate 108 is not reduced. Thus, in this prior art example, the beam 104 travels in its entirety from the light source 102 to the substrate 108.

FIG. 3 shows the path of travel for a light beam for the system shown in FIG. 1. This is a front view, which looks at the system from the left side of FIG. 2. Again, for illustrative purposes only, the cross sectional areas 202, 204 and the substrate 108 are shown in a slight isometric configuration. In this view, the beam 104 approaches the mirror 106B from above the page. The beam 104 reflects off of the mirror 106B toward the substrate 108. The beam 104 is not reduced as it travels from the light source 102 to the substrate 108.

It should also be apparent from the prior art system shown in FIG. 1 that the beam 104 that reflects off of the substrate 108 is not reduced in its cross-sectional area before it reaches the photodetector 110.

In an apparatus used to characterize structures using reflectance spectrophotometry, it is desirable that light reflected from the material is directed into a spectrophotometer by an optical relay that has a minimum of aberrations. First, it is desirable to eliminate the chromatic aberrations to achieve an accurate measurement. However, lenses and mirrors have other, nonchromatic aberrations as well. These aberrations include spherical aberration, coma, astigmatism, curvature of field, and distortion. All lenses and mirrors suffer from these aberrations to some extent, even if they are perfectly machined. The existence of these aberrations represents a fundamental limitation on the nature of a lens or mirror—a limitation that is generally neglected in the paraxial approximation of introductory texts. Since the structures of interest often are patterned structures, such as integrated circuits, diffraction gratings, or contact holes, the structures usually are small and the areas that they are comprised of are small. Consequently, the measurement area is desirably small enough to fit within the entire pattern, yet large enough so that there are repeating structures in the measurement area. Thus, it is desirable that a reflectance spectrophotometric apparatus be able to image a small area, on the order of 50 microns in diameter, of the area of interest to a spectrophotometer with as little aberration as possible. It is also desirable that the apparatus include hardware for translating the target with respect to the imaging optics so that different regions of the target may be characterized.

One disadvantage for systems that use larger angles of incidence is that they do not correctly measure trenches with high aspect ratios (i.e. deep and narrow). With these systems it is possible that the incoming light will not reach the bottom of the trench before striking a wall. This effect is sometimes referred to as "shadowing." In order to obtain an accurate measurement, is it desirable that the beam strikes the bottom of the trench and reflect out of the trench without hitting the side walls of the trench.

Another disadvantage for systems that use larger angles of incidence is that they take more time to determine structure geometries when the trenches of the geometry in question are parallel to the plane of the angle of incidence. In order to speed the calculation time, smaller angles of incidence can be used.

Thus, it is desirable for a reflective spectrophotometric device to have an angle of incidence that is small.

SUMMARY

This document describes a system that characterizes structures of a sample. The system includes a light source and mirrors for directing and collecting light. The angle of incidence for the collected light is small.

DESCRIPTION

The measurement system described in this application has several advantages over the prior art. First of all, by using a small angle of incidence for the beam of light, the calculations required to determine the properties of the sample are greatly diminished for diffraction gratings. Fewer calculations mean a faster processing time. It has been said in the past that time is money, and, in a manufacturing or evaluation situation, this axiom is particularly true. Another advantage to the small angle of incidence system is that the accuracy goes up as the angle of incidence diminishes. In addition, the "shadowing" effect (mentioned above) can be reduced or eliminated with small angles. Where some prior art systems might have measured a sample from a variety of angles of incidence in order to improve the overall accuracy of the system, the disclosed measurement system has proven to be at least as accurate, and in most cases more accurate, than the prior art while using only one angle of incidence for measurement purposes. The combination of only needing one measurement angle and a faster processing time for that one angle leads to dramatic increases in productivity.

Figure 1:
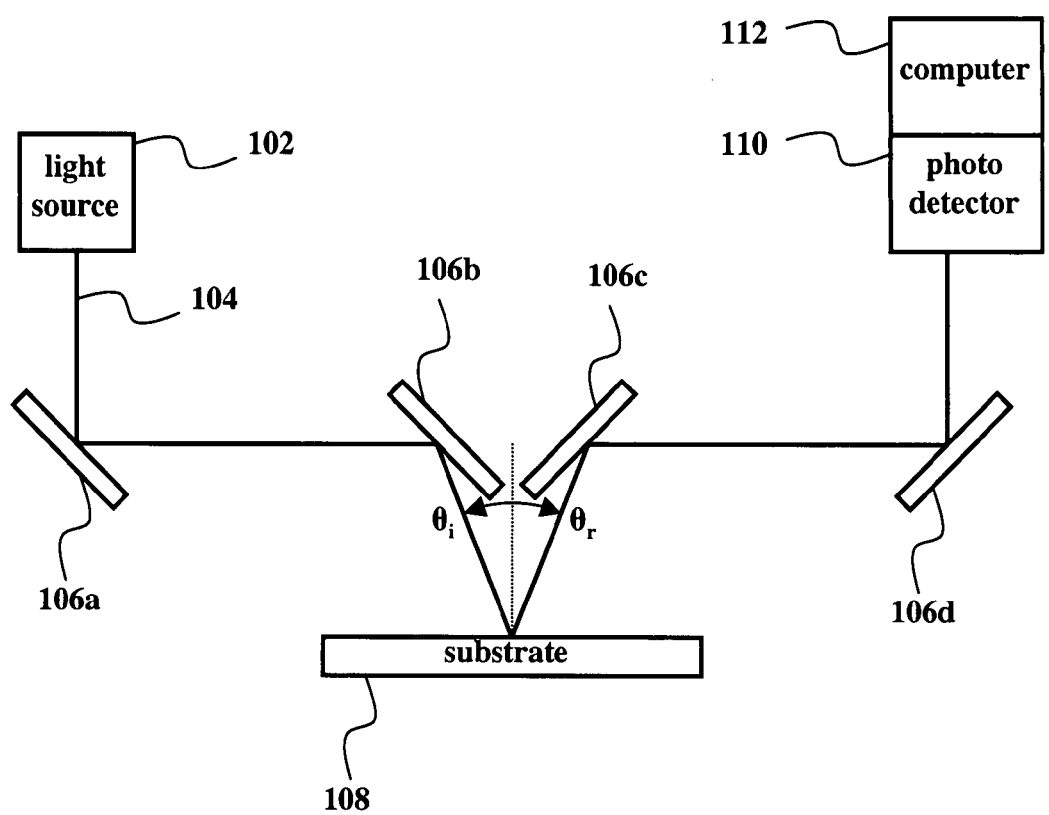
FIG. 1 shows a prior art measurement system.
Figure 2:
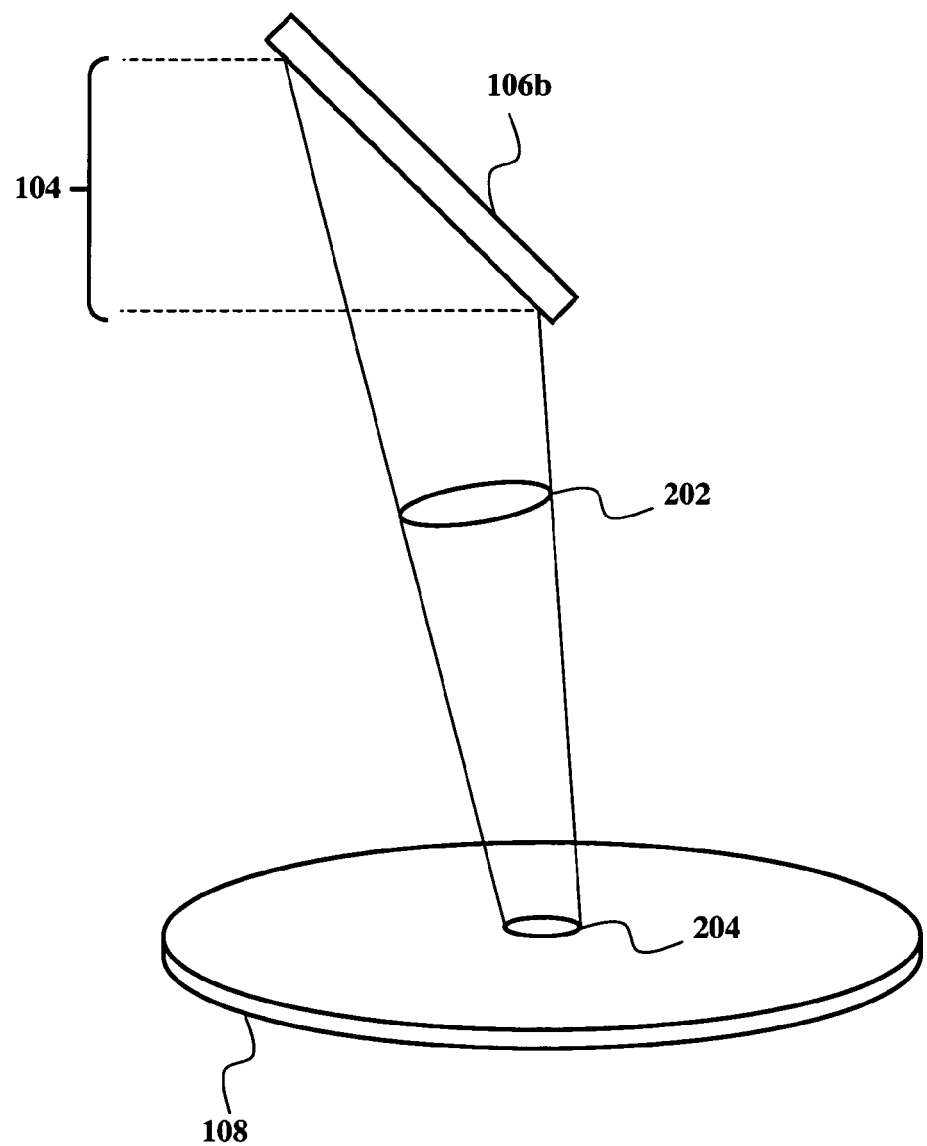
FIG. 2 shows a prior art path of travel for a light beam.
Figure 4:
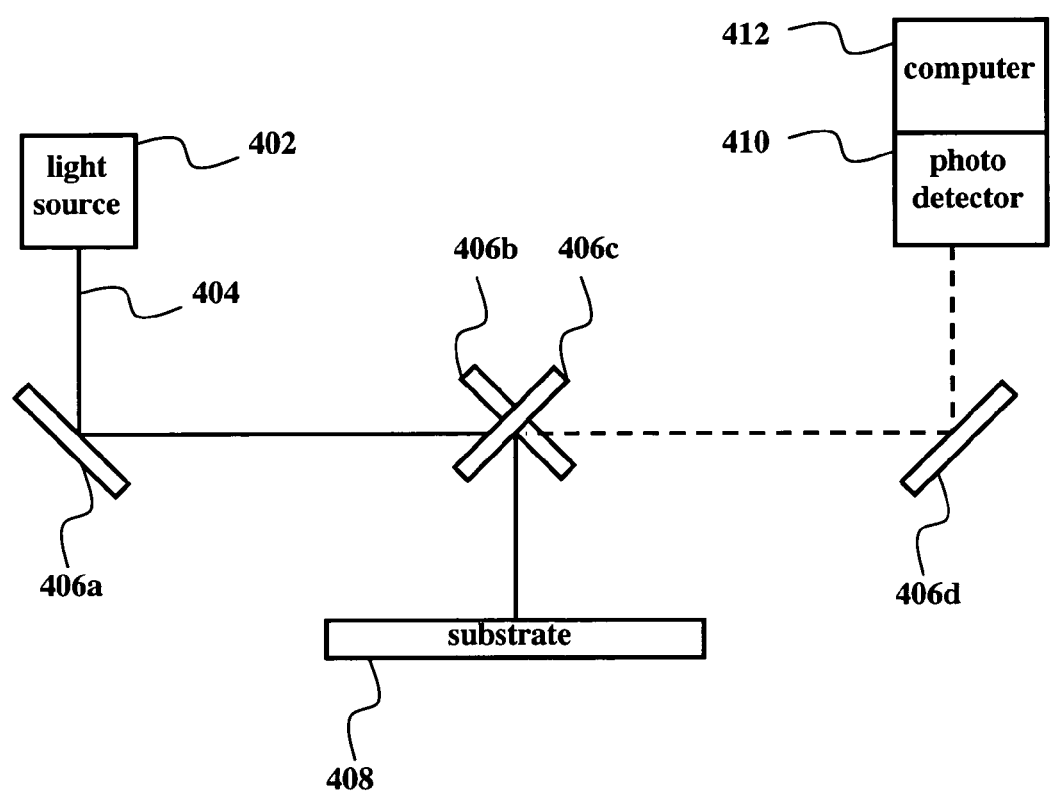
FIG. 4 shows an example of a reflective spectrophotometric system.

FIG. 4 shows an example of a reflective spectrophotometric system. In this example, which is a side view, a light source 402 emits a beam 404 of light. The beam 404 is directed to the substrate 408 with two mirrors 406A, B. The beam 404 is directed to the photodetector 410, which is a spectrophotometer, with two mirrors 406C, D. In this side view, the beam 404 appears to travel either parallel with or perpendicular to the surface of the substrate 408. This is in contrast to the prior art shown in FIG. 1, where the beam 104 travels at a non-perpendicular angle toward the substrate 108 and away from the substrate 108.

Figure 5:
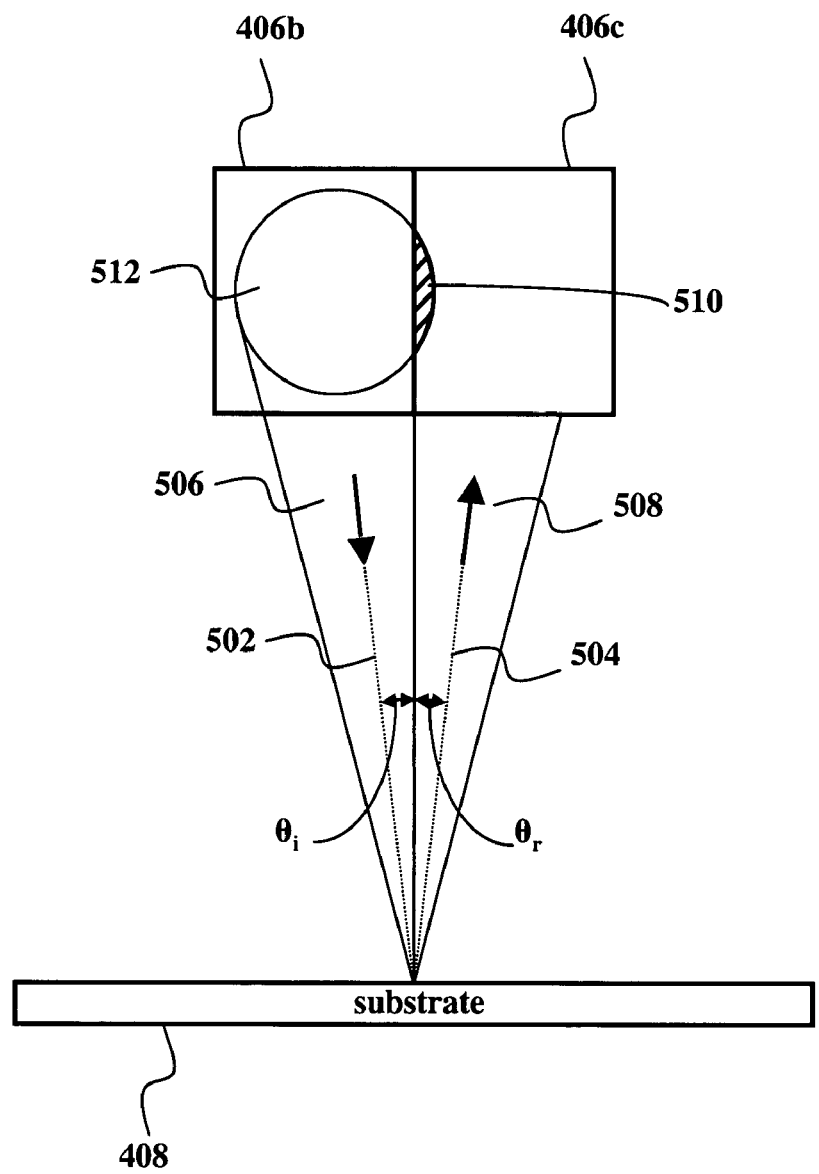
FIG. 5 shows an example of the path of travel for a light beam.

FIG. 5 shows a front view of some of the elements shown in FIG. 4. This view shows what might be seen from the left side of the page from FIG. 4. The beam 404 reflects off of the mirror 406B toward the substrate 408. The cross sectional area of the beam 404 comprises two parts: the reflected portion 512 and the discarded portion 510. The discarded portion 510 is marked with crosshatching. The discarded portion 510, in this example, strikes the backside of the mirror 406C, and is discarded. The reflected portion 512 continues through the system. The central axes of the incident beam 502 and the central axis of the reflected beam 504 are shown. The angle of incidence $\theta_i$ is measured from the normal to the substrate 408 to the central axis 502. Likewise, the angle of reflectance $\theta_r$ is measured from the normal of the substrate 408 to the central axis 504. Also shown are the conical beam sections which includes the incident conical beam section 506 and the reflective conical beam section 508. These sections 506, 508 are not truly conical in this case, due to the discarded portion 510. Arrows are shown to indicate the path of travel of the beam 404.

Figure 3:
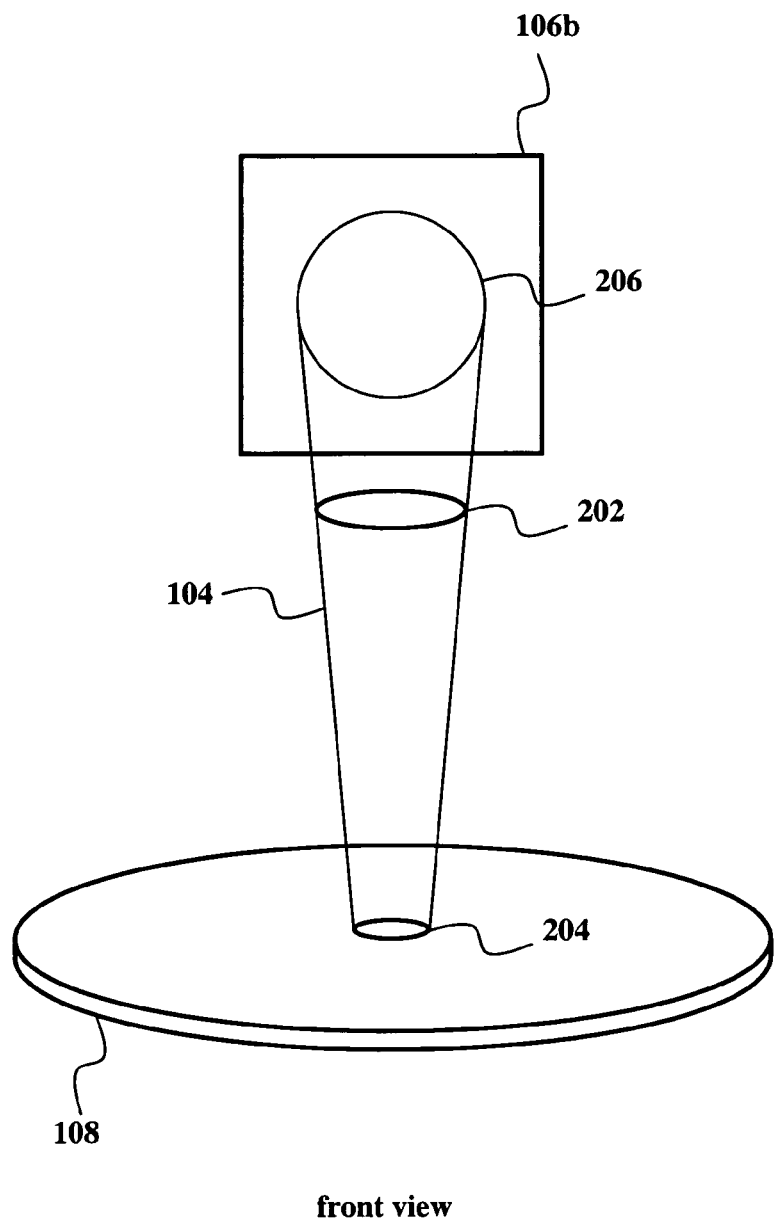
FIG. 3 shows a prior art path of travel for a light beam.

One will note that the prior art example shown in FIG. 3 shows the cross sectional area of the beam 104 fully intact. Furthermore, the beam 104 in FIG. 3 approaches the substrate 108 perpendicular to the substrate 108 in that front view. In contrast, FIG. 5 shows the beam 404 with an angle of incidence and angle of reflectance in the front view.

The mirrors 406 B, C are desirably of a size and distance from the substrate 408 in order to achieve a proper illumination spot size, while achieving a small cone angle. The trade off between spot size and cone angle left for the engineer to determine, depending on the requirements of the system.

The angle of incidence is also balanced with discarding a portion of the beam. The smaller the angle of incidence, the larger the discarded portion 510. Thus, there is a balancing act between the amount of light propagated through the system versus the angle of incidence relative to the substrate 408. The more light, the better the signal and the better the measurement. But, as is discussed above, the smaller the angle of incidence, the faster and more accurate the analysis (for certain types of structures). A good compromise has been found to be an angle of incidence of about 3.5° or less. When central axes 502, 504 have an angle of about 3.5°, the weighted average angle of incidence of any particular path of travel is roughly 4°. This makes it possible for the system to perform nearly as well as normal incidence beam system.

In this application, further discussion of angles of incidence or reflectance refer to the angle between the central axis of the beam 404 relative to the normal of the substrate 408 (or sample).

Figure 6:
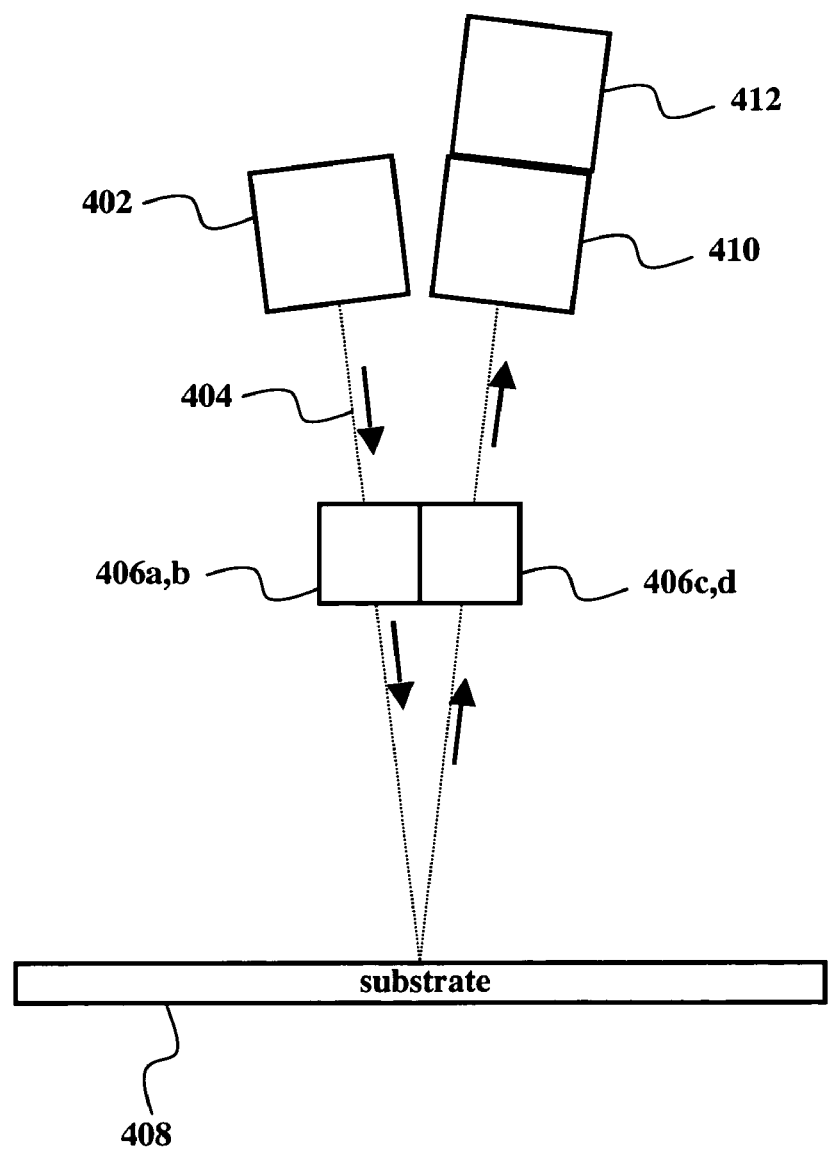
FIG. 6 shows an example of the path of travel for a light beam.

FIG. 6 shows an example of components laid out in the system. In this example, the light source 402 emits the beam 404 at an angle that is about the same as the angle of incidence relative to the substrate 408. Likewise, the photo detector 410 is configured to receive the beam 404 at an angle that is about the same as the angle of reflectance relative to the substrate 408. Thus, the mirrors 406A, B, C, D need only translate the beam 404 relative to the plane of the page of FIG. 6.

The mirrors shown in FIGS. 4-6 may be toroidal mirrors or off-axis parabolic mirrors. A mirror pair works as an optical relay. Toroidal pairs have the advantage of virtually eliminating chromatic aberrations and minimizing non-chromatic aberrations. It may be possible to build a system where the light source 402 emits the beam 404 in such a manner that only one mirror 406B is required to direct the beam 404 toward the substrate 408. Another possibility might be to build a system where the photodetector 410 can receive the beam 404 directly after it reflects off of the mirror 406C. In order to obtain the properly shaped mirrors 406B, C, one would normally cut oversized toroidal mirrors to the appropriate shape.

Off-axis parabolic mirrors offer certain advantages compared to toroidal mirrors. An off-axis parabolic mirror can exactly collimate light from an off axis point, whereas a toroidal mirror cannot precisely collimate the light. A pair of toroidal mirrors cancels most of the axial aberration present. However, a pair of toroidal mirrors may not correct the aberrations of off-axis points. Off-axis parabolic mirrors that share a common axis generally have low axial and off axis aberrations, with the foci generally being on the same axis. If off-axis parabolic mirrors can be purchased "off the shelf," then there can be significant cost savings.

Off-axis parabolic mirrors have certain disadvantages compared to toroidal mirrors. The addition of flat folding mirrors is usually needed to fit into the optical system. The additional mirrors reduce the signal throughout the system. Off-axis parabolic mirrors with offset axes generally have low axial but very large off-axis aberrations.

It has been geometrically shown that the angle of incidence can go as low as 7° (for a cone angle of 14° and a spot size of 50 μm, for example) without having the cross sectional area of the beam 404 reduced. For angles of 6° or less, the mirrors 406B, C would normally interfere with each other. The discarded portion 510 comprises 2%, 3.5%, 5.3%, 7.2%, 9.5%, and 12% of the cross sectional area of the beam 404 when the angle of incidence is 4.5°, 4.25°, 4.0°, 3.75°, 3.5°, and 3.25° respectively.

Measurements of orthogonal geometries, such as gratings, can vary with the angle of incidence. When the trenches of the geometry in question are parallel to the plane of the angle of incidence, smaller angles of incidence translate to faster calculations. The plane of the angle of incidence is defined by the angle of incidence and the normal of the surface. It has been observed that when these angles are 5° or less that speed gains are observed. When the trenches of the geometry in question are perpendicular to the plane of the angle of incidence, there is not an appreciable difference in calculation time with respect to angles of incidence.

Figure 7:
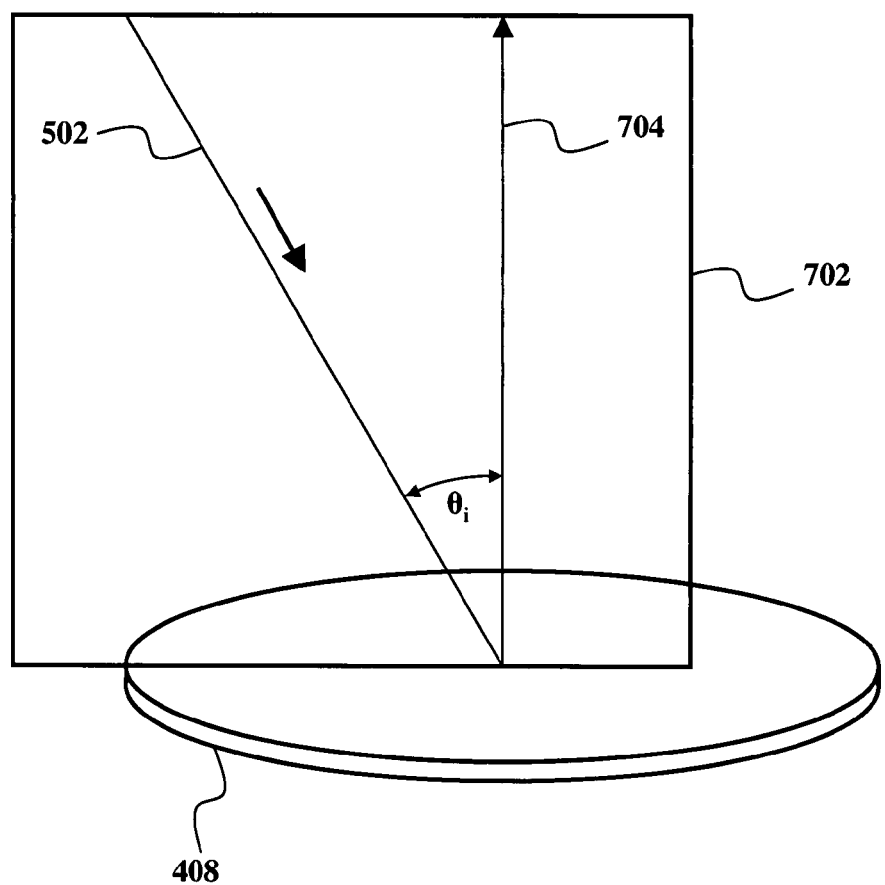
FIG. 7 shows an example of the plane of the angle of incidence.

FIG. 7 shows an example of the plane of the angle of incidence. The plane 702 is defined by the axis of incident light 502 and the normal to the substrate 704.

Figure 8:
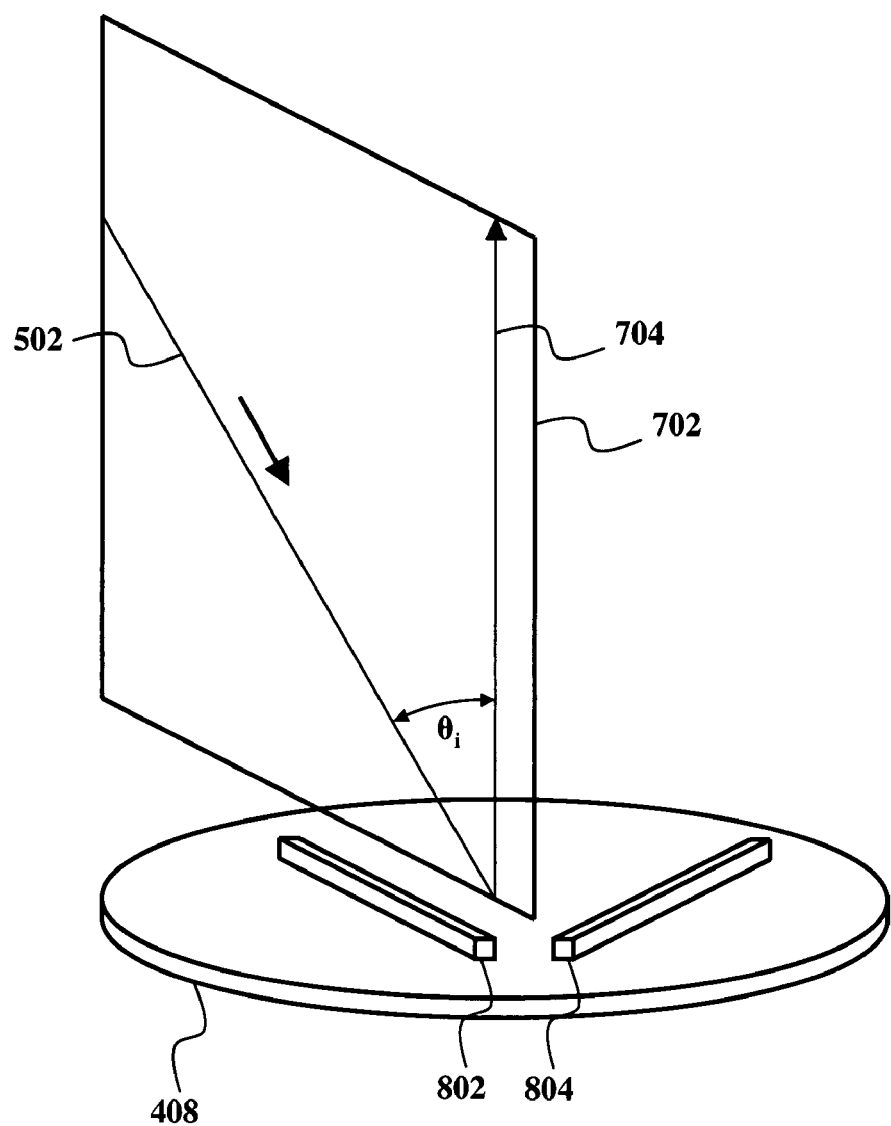
FIG. 8 shows an example of the plane of the angle of incidence relative to features that are being measured.

FIG. 8 shows an example of the plane of the angle of incidence relative to features that are being measured. In this example there are two protrusions 802, 804. The first protrusion 802 is parallel to the plane 702. The second protrusion 804 is perpendicular to the plane 702. When the angle of incidence is small, calculations regarding features that are parallel to the plane 702 (protrusion 802 for example) are easier and faster than when the angle of incidence is large.

Figure 9:
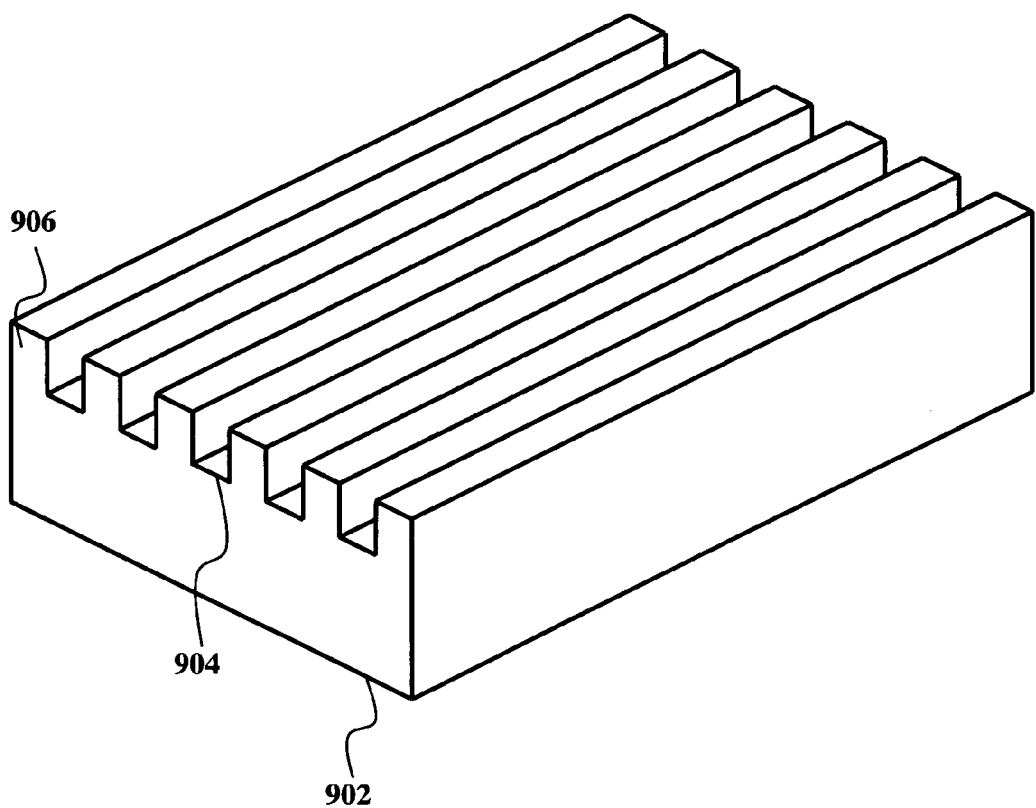
FIG. 9 shows an example of a diffraction grating.

FIG. 9 shows an example of a diffraction grating. The diffraction grating 902 has several trenches 904. From the point of view of the bottom of the trenches 904, there are several protrusions 906. Thus, if a length of either a trench 904 or a protrusion 906 is parallel, or roughly parallel, to the plane of the angle of incidence 702 and the angle of incidence is small, then the critical dimension calculation time is faster.

It is also possible to use a beam splitter to direct the light to and from the sample. The disadvantage of using a beam splitter is that 75% of the light is lost by either for flexion or passthrough in the undesired direction. The advantage is that the angle of incidence is 0°. Thus, using a beam splitter allows one to achieve the fastest possible calculation times for certain types of structures and allow more accurate measurement for structures with high aspect ratios (depth to opening).

It will be apparent to one skilled in the art that the described embodiments may be altered in many ways without departing from the spirit and scope of the invention. Accordingly, the scope of the invention should be determined by the following claims and their equivalents.

What is claimed is:

1. A system for characterizing optical properties of a sample, the system comprising:
a light source for generating a broadband optical beam;
a first mirror positioned to image the light source on the sample; and
a second mirror positioned to collect light reflected by a measurement area of the sample,
wherein an angle of incidence of light directed to the sample is $\theta_1$, where $0° \leq \theta_1 \leq 3.5°$, and wherein (i) the first mirror is shaped such that at least 9.5% of a conical light beam is not reflected by the first mirror, (ii) the second mirror is shaped such that at least 9.5% of a conical light beam is not reflected by the second mirror, (iii) the first mirror is shaped and positioned such that at least 9.5% of a cross sectional area of a light beam is not reflected by the first mirror, (iv) the second mirror is shaped and positioned such that at least 9.5% of a cross sectional area of a light beam is not reflected by the second mirror.

2. A method of measuring structures comprising:
directing a beam of light onto a target, the beam having an angle relative to a substrate, the angle of being $\theta_1$, where $0 \leq \theta_1 \leq 3.5°$;
collecting light that is reflected off of the substrate;
discarding a portion of the reflected light;
directing the reflected light into a spectrophotometer; and
providing structure dimensions of the substrate based on readings from the spectrophotometer
where a feature of interest is parallel to a plane, the plane being defined by the angle of incidence and a normal to the target.

3. The method of claim 2, wherein the feature of interest is a trench.

4. The method of claim 2, wherein the feature of interest is a protrusion.

5. A system for characterizing optical properties of a sample, the system comprising:
a light source for generating a broadband optical beam;
first and second toroidal mirrors positioned to image the light source on the sample; and
third and forth toroidal mirrors positioned to collect and direct light reflected by a measurement area of the sample;
a spectrophotometer, the spectrophotometer receiving the collected light; and
a computer, the computer analyzing data collected from the spectrophotometer in order to determine optical properties of the sample;
wherein an angle of incidence of light directed to the sample is $\theta_1$, where $0° \leq \theta_1 \leq 3.5°$,
wherein an angle of reflection of light collected from the sample is $\theta_2$, where $0° \leq \theta_2 \leq 3.5°$,
wherein mirrors immediately before and after the sample are shaped such that at least 9.5% of a conical light beam is not reflected.

* * * * *